US009255879B2

(12) United States Patent
Sugimoto

(10) Patent No.: US 9,255,879 B2
(45) Date of Patent: Feb. 9, 2016

(54) METHOD OF MEASURING REFRACTIVE INDEX DISTRIBUTION, METHOD OF MANUFACTURING OPTICAL ELEMENT, AND MEASUREMENT APPARATUS OF REFRACTIVE INDEX DISTRIBUTION

(71) Applicant: CANON KABUSHIKI KAISHA, Tokyo (JP)

(72) Inventor: Tomohiro Sugimoto, Yoshikawa (JP)

(73) Assignee: CANON KABUSHIKI KAISHA (JP)

( * ) Notice: Subject to any disclaimer, the term of this patent is extended or adjusted under 35 U.S.C. 154(b) by 161 days.

(21) Appl. No.: 13/923,580

(22) Filed: Jun. 21, 2013

(65) Prior Publication Data

US 2014/0009765 A1  Jan. 9, 2014

(30) Foreign Application Priority Data

Jul. 9, 2012  (JP) .................................. 2012-154073

(51) Int. Cl.
| | |
|---|---|
| G01N 21/21 | (2006.01) |
| G01N 21/41 | (2006.01) |
| G01N 21/45 | (2006.01) |
| B29D 11/00 | (2006.01) |
| G01M 11/02 | (2006.01) |

(52) U.S. Cl.
CPC .......... *G01N 21/41* (2013.01); *B29D 11/00951* (2013.01); *G01N 21/45* (2013.01); *G01M 11/0242* (2013.01)

(58) Field of Classification Search
CPC ....... G01N 21/41; G01N 21/45; G01M 11/00; G01M 11/0242
See application file for complete search history.

(56) References Cited

U.S. PATENT DOCUMENTS

| | | | | |
|---|---|---|---|---|
| 3,966,311 | A * | 6/1976 | Korn et al. | 351/159.61 |
| 4,634,233 | A * | 1/1987 | Usami | G02B 3/0087 359/654 |
| 5,223,862 | A * | 6/1993 | Dasher et al. | 351/159.62 |
| 5,333,052 | A * | 7/1994 | Finarov | 356/369 |
| 6,196,684 | B1 * | 3/2001 | Comte et al. | 351/159.41 |
| 6,424,414 | B1 * | 7/2002 | Weiland et al. | 356/239.4 |
| 2004/0036858 | A1 * | 2/2004 | Biel et al. | 356/124 |
| 2007/0188741 | A1 * | 8/2007 | Fleischmann et al. | 356/124 |

(Continued)

FOREIGN PATENT DOCUMENTS

| | | |
|---|---|---|
| JP | 08-122210 A | 5/1996 |
| JP | 2012-088342 A | 5/2012 |

*Primary Examiner* — Gregory J Toatley
*Assistant Examiner* — Maurice Smith
(74) *Attorney, Agent, or Firm* — Rossi, Kimms & McDowell LLP

(57) ABSTRACT

A method of measuring a refractive index distribution includes steps of setting a plurality of different arrangements by a translation movement in a state where an object is arranged in first and second media having refractive indices different from a refractive index of the object, measuring transmissive wavefront of the object for each of media and each of the plurality of arrangements by reference light entering the object (S400), obtaining wavefront aberration corresponding to a difference between each transmissive wavefront and a reference transmissive wavefront (S500), obtaining refractive index distribution of the object by removing an influence of a shape error of the object using wavefront aberration of two media in which the object is arranged at the same position (S70), and obtaining refractive index distribution information of the object based on a plurality of refractive index distributions corresponding to the plurality of arrangements (S80).

20 Claims, 4 Drawing Sheets

(56) References Cited

U.S. PATENT DOCUMENTS

2010/0165355 A1* 7/2010 Kato .............................. 356/517
2011/0116081 A1* 5/2011 Sugimoto ..................... 356/128
2011/0292379 A1* 12/2011 Kato .............................. 356/128
2012/0069350 A1* 3/2012 Sugimoto ..................... 356/517
2012/0241989 A1* 9/2012 Sugimoto ...................... 264/1.1
2012/0249749 A1* 10/2012 Stavnitzky et al. ............. 348/47

* cited by examiner

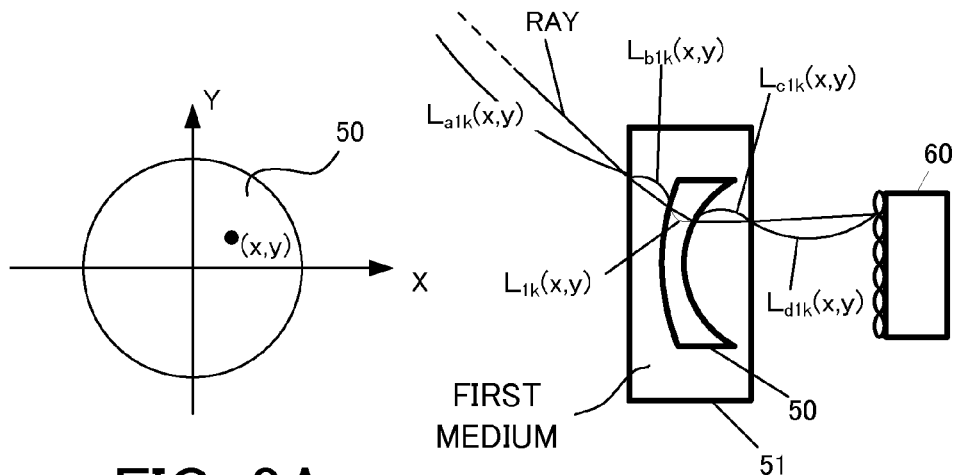
FIG. 3A
FIG. 3B
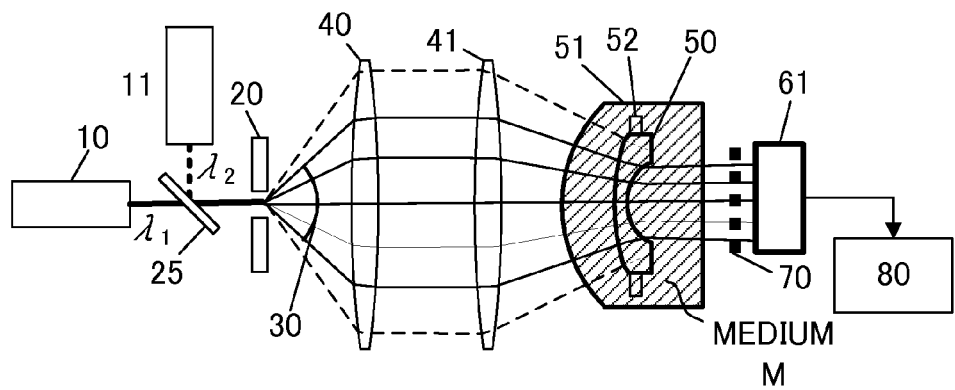
FIG. 4A
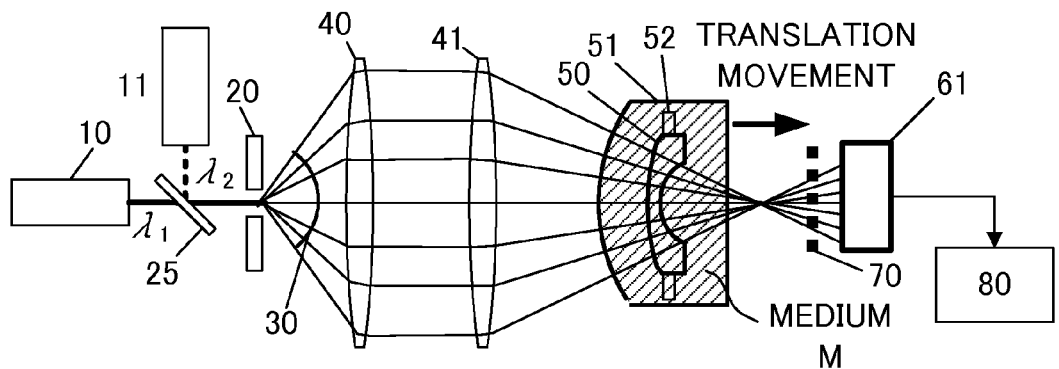
FIG. 4B

METHOD OF MEASURING REFRACTIVE INDEX DISTRIBUTION, METHOD OF MANUFACTURING OPTICAL ELEMENT, AND MEASUREMENT APPARATUS OF REFRACTIVE INDEX DISTRIBUTION

BACKGROUND OF THE INVENTION

1. Field of the Invention

The present invention relates to a method of measuring a refractive index distribution that measures the refractive index distribution of an object.

2. Description of the Related Art

Japanese Patent Laid-Open No. H08-122210 discloses a method of obtaining a refractive index distribution of an object by measuring a transmissive wavefront while rotating the object at various angles in a state where the object is immersed in a test solution (matching oil) having a refractive index nearly equal to that of the object. Japanese Patent Laid-Open No. 2012-088342 discloses a method of obtaining the refractive index distribution of an object having a high refractive index by measuring the transmissive wavefront while rotating the object at various angles in a state where the object is immersed in two kinds of media having different refractive indices for the object.

In the method of the method disclosed in Japanese Patent Laid-Open No. H08-122210, the matching oil having substantially the same refractive index as that of the object is necessary. However, the matching oil having the high refractive index has a low transmittance and a small signal can only be obtained from a detector, and therefore a measurement accuracy of the object having the high refractive index is deteriorated. Furthermore, the method disclosed in Japanese Patent Laid-Open No. 2012-088342 is assumed that a position or an inclination of the object in rotating the object around an axis perpendicular to an optical axis is previously known. However, an actual shape of the object is different from a design value, and therefore it is difficult to specify the position or the inclination of the object with high accuracy when rotating the object.

BRIEF SUMMARY OF THE INVENTION

The present invention provides a method of measuring a refractive index distribution and a measurement apparatus of the refractive index distribution that are capable of measuring the refractive index distribution of an object with high accuracy. The present invention also provides a method of measuring an optical element using the method of measuring the refractive index distribution.

A method of measuring a refractive index distribution as one aspect of the present invention includes a measurement step of arranging an object in a medium having a refractive index different from a refractive index of the object so as to measure a transmissive wavefront of the object by reference light entering the object, and a calculation step of calculating a refractive index distribution of the object using a measurement result of the transmissive wavefront. In the measurement step, a translation movement of the object is performed with respect to the reference light so as to set a plurality of arrangements of the object different from each other, and for the plurality of arrangements, a first transmissive wavefront in a first medium having a first refractive index and a second transmissive wavefront in a second medium having a second refractive index different from the first refractive index are measured. In the calculation step, a first wavefront aberration that is a difference between a measurement result of the first transmissive wavefront and a transmissive wavefront obtained when a reference object that has the same shape as the object and that has a specific refractive index distribution has the same arrangement as the object in the first medium is calculated for the plurality of arrangements, a second wavefront aberration that is a difference between a measurement result of the second transmissive wavefront and a transmissive wavefront obtained when the reference object has the same arrangement as the object in the second medium is calculated for the plurality of arrangements, and the refractive index distribution of the object for each of the plurality of arrangements is obtained while removing a shape component of the object based on the first wavefront aberration and the second wavefront aberration so as to calculate the refractive index distribution of the object based on a plurality of refractive index distributions corresponding to the plurality of arrangements.

A method of measuring a refractive index distribution as another aspect of the present invention includes a measurement step of arranging an object in a medium having a refractive index different from a refractive index of the object so as to measure a transmissive wavefront of the object by reference light entering the object, and a calculation step of calculating a refractive index distribution of the object using a measurement result of the transmissive wavefront. In the measurement step, a translation movement of the object is performed with respect to the reference light so as to set a plurality of arrangements of the object different from each other, and for the plurality of arrangements, a first transmissive wavefront for a first wavelength and a second transmissive wavefront for a second wavelength different from the first wavelength are measured. In the calculation step, a first wavefront aberration that is a difference between a measurement result of the first transmissive wavefront and a transmissive wavefront for the first wavelength obtained when a reference object that has the same shape as the object and that has a specific refractive index distribution has the same arrangement as the object in the medium is calculated for the plurality of arrangements, a second wavefront aberration that is a difference between a measurement result of the second transmissive wavefront and a transmissive wavefront for the second wavelength obtained when the reference object has the same arrangement as the object in the medium is calculated for the plurality of arrangements, and the refractive index distribution of the object for each of the plurality of arrangements is obtained while removing a shape component of the object based on the first wavefront aberration and the second wavefront aberration so as to calculate the refractive index distribution of the object based on a plurality of refractive index distributions corresponding to the plurality of arrangements.

A method of manufacturing an optical element as another aspect of the present invention includes the steps of molding the optical element, and measuring a refractive index distribution of the optical element using the method of measuring the refractive index distribution according to claim 1 so as to evaluate the molded optical element.

A measurement apparatus of a refractive index distribution as another aspect of the present invention includes a light source, an object case configured to contain an object and a medium having a refractive index different from a refractive index of the object, a moving unit configured to perform a translation movement of the object with respect to reference light entering the object, a measuring unit configured to measure a transmissive wavefront of the object arranged in the medium using light from the optical source, and a processing unit configured to obtain a refractive index distribution of the object based on the transmissive wavefront. The translation movement of the object is performed by the moving unit so as to set a plurality of arrangements of the object different from each other, and a first transmissive wavefront in a first medium having a first refractive index and a second transmissive wavefront in a second medium having a second refractive index for the plurality of arrangements are measured by the measuring unit. The processing unit is configured to calculate a first wavefront aberration that is a difference between a measurement result of the first transmissive wavefront and a transmissive wavefront obtained when a reference object that has the same shape as the object and that has a specific refractive index distribution has the same arrangement as the object in the first medium for the plurality of arrangements, calculate a second wavefront aberration that is a difference between a measurement result of the second transmissive wavefront and a transmissive wavefront obtained when the reference object has the same arrangement as the object in the second medium for the plurality of arrangements, and obtain the refractive index distribution of the object for each of the plurality of arrangements while removing a shape component of the object based on the first wavefront aberration and the second wavefront aberration so as to calculate the refractive index distribution of the object based on a plurality of refractive index distributions corresponding to the plurality of arrangements.

A measurement apparatus of a refractive index distribution as another aspect of the present invention includes a light source configured to emit lights having first and second wavelengths, an object case configured to contain an object and a medium having a refractive index different from a refractive index of the object, a moving unit configured to perform a translation movement of the object with respect to reference light entering the object, a measuring unit configured to measure a transmissive wavefront of the object arranged in the medium using light from the optical source, and a processing unit configured to obtain a refractive index distribution of the object based on a first transmissive wavefront and a second transmissive wavefront measured by using the first and second wavelengths respectively. The translation movement of the object is performed by the moving unit so as to set a plurality of arrangements of the object different from each other, and each of the first transmissive wavefront and the second transmissive wavefront for the plurality of arrangements is measured by the measuring unit. The processing unit is configured to calculate a first wavefront aberration that is a difference between a measurement result of the first transmissive wavefront and a transmissive wavefront for the first wavelength obtained when a reference object that has the same shape as the object and that has a specific refractive index distribution has the same arrangement as the object in the medium for the plurality of arrangements, calculate a second wavefront aberration that is a difference between a measurement result of the second transmissive wavefront and a transmissive wavefront for the second wavelength obtained when the reference object has the same arrangement as the object in the medium for the plurality of arrangements, and obtain the refractive index distribution of the object for each of the plurality of arrangements while removing a shape component of the object based on the first wavefront aberration and the second wavefront aberration so as to calculate the refractive index distribution of the object based on a plurality of refractive index distributions corresponding to the plurality of arrangements.

Further features and aspects of the present invention will become apparent from the following description of exemplary embodiments with reference to the attached drawings.

BRIEF DESCRIPTION OF THE DRAWINGS

FIGS. 3A and 3B are diagrams of illustrating a coordinate system defined on the object and an optical path of a ray in a first medium inside the measurement apparatus, respectively in Embodiment 1.

FIGS. 4A and 4B are block diagrams of a measurement apparatus of a refractive index distribution in Embodiment 2.

DETAILED DESCRIPTION OF THE PREFERRED EMBODIMENTS

Figure 1A:
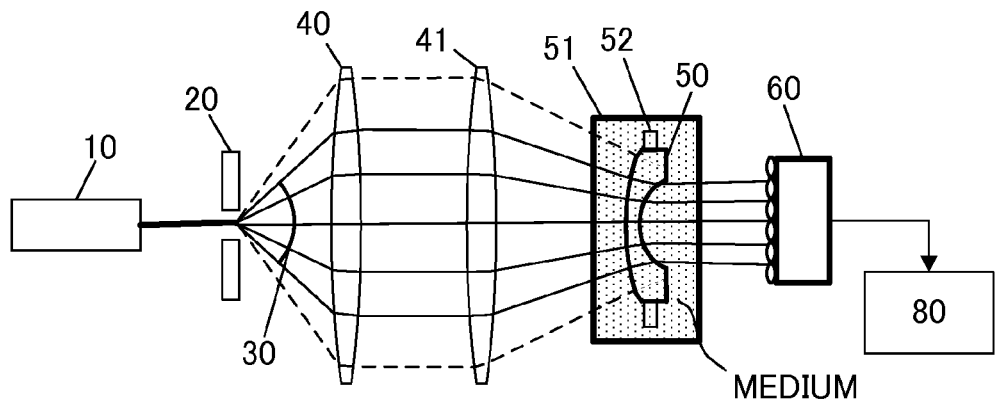
FIGS. 1A and 1B are block diagrams of a measurement apparatus of a refractive index distribution in Embodiment 1.

Exemplary embodiments of the present invention will be described below with reference to the accompanied drawings. In the drawings, the same elements will be denoted by the same reference numerals and the descriptions thereof will be omitted.

[Embodiment 1]

Figure 1B:
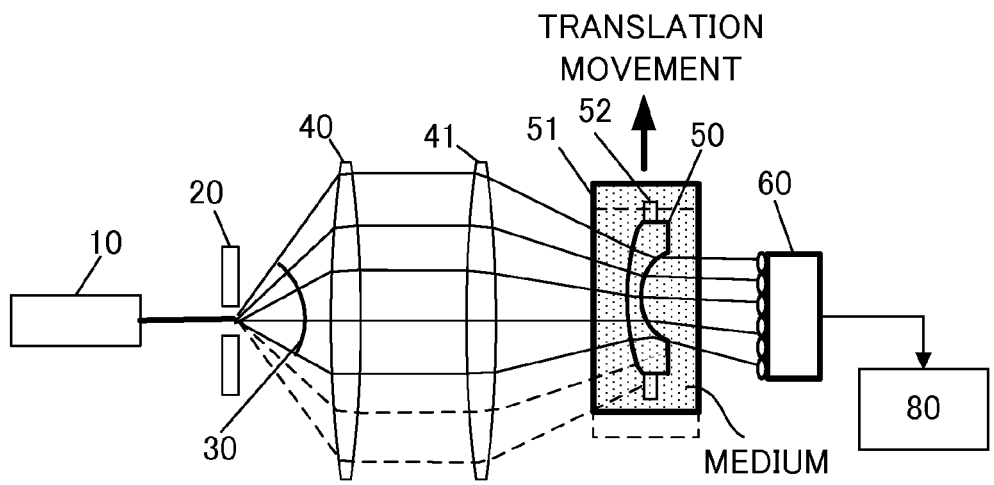

First of all, referring to FIGS. 1A, 1B, 2, 3A, and 3B, Embodiment 1 of the present invention will be described. FIGS. 1A and 1B are block diagrams of a measurement apparatus of a refractive index distribution in the present embodiment. The measurement apparatus of the refractive index distribution of the present embodiment, first of all, makes reference light enter an object so as to measure a transmissive wavefront in a state where the object is disposed in each of two kinds of media (for example, water and oil) that has a refractive index different from a refractive index of the object (a measurement step). The two kinds of media are a first medium that has a first refractive index and a second medium that has a second refractive index. Subsequently, the measurement apparatus uses a measurement result of the transmissive wavefront so as to calculate a refractive index distribution of the object (a calculation step). In this case, a translation movement of the object is performed with respect to the reference light, and a plurality of arrangements in which the arrangements of the object are different from each other are set so as to obtain the refractive index distribution for each arrangement. Then, based on a plurality of refractive index distributions corresponding to the plurality of arrangements, the refractive index distribution of the object (preferably, a refractive index distribution over the whole region of an effective diameter of the object) is calculated. In the present embodiment, as the refractive index distribution of the object, a three-dimensional refractive index distribution can also be calculated.

An object 50 is, for example, a lens (an optical element) that has a negative power. A side surface of an object case 51 is made of a material through which light transmits (for example, a glass). The object case 51 contains the medium and the object 50 that is held by an object supporting portion 52. The object case 51 includes a moving unit such as a stage capable of performing the translation movement. In the present embodiment, as a measuring unit of the transmissive wavefront, a Shack-Hartmann sensor 60 is used.

Light emitted from a light source 10 (for example, a semiconductor laser) in FIGS. 1A and 1B is diffracted by a pinhole 20 so as to be divergent light. Reference light 30 that is the divergent light passes through a collimator lens 40 and a collimator lens 41 so as to be convergent light. A part of the convergent light passes through the medium inside the object case 51 so as to enter the object 50. On the other hand, a part of the light is blocked by an edge portion of the object 50, the object case 51, or the object supporting portion 52. The reference light 30 transmits through the object 50, and then becomes substantially parallel light so as to enter the Shack-Hartmann sensor 60. In the present embodiment, a direction in which the light (the light beam) of the light source 10 is emitted is referred to as an optical axis direction, and a center of the light beam is referred to as an optical axis.

FIG. 1A illustrates an optical arrangement when the light transmitting through the object 50 is nearly the parallel light. Outer light of the convergent light emitted from the collimator lens 41 is blocked by the edge portion of the object 50. In accordance with characteristics of the object 50, even when the light passes through an inside of the effective diameter of a front surface of the object 50, there is a case where the light illuminates the edge portion of the object and thus the light does not pass through the object 50. In other words, there is an object for which a whole of the effective diameter (the whole region of the effective diameter) of the object 50 cannot be measured by one measurement. In this case, as described in the present embodiment, the refractive index distribution for the whole region of the effective diameter of the object 50 may be calculated using the plurality of refractive index distributions obtained for the plurality of arrangements as described in the present embodiment. The effective diameter of the object means a value that defines a use region of the object based on a diameter (or a radius) of each of a first surface and a second surface of the object.

Figure 2:
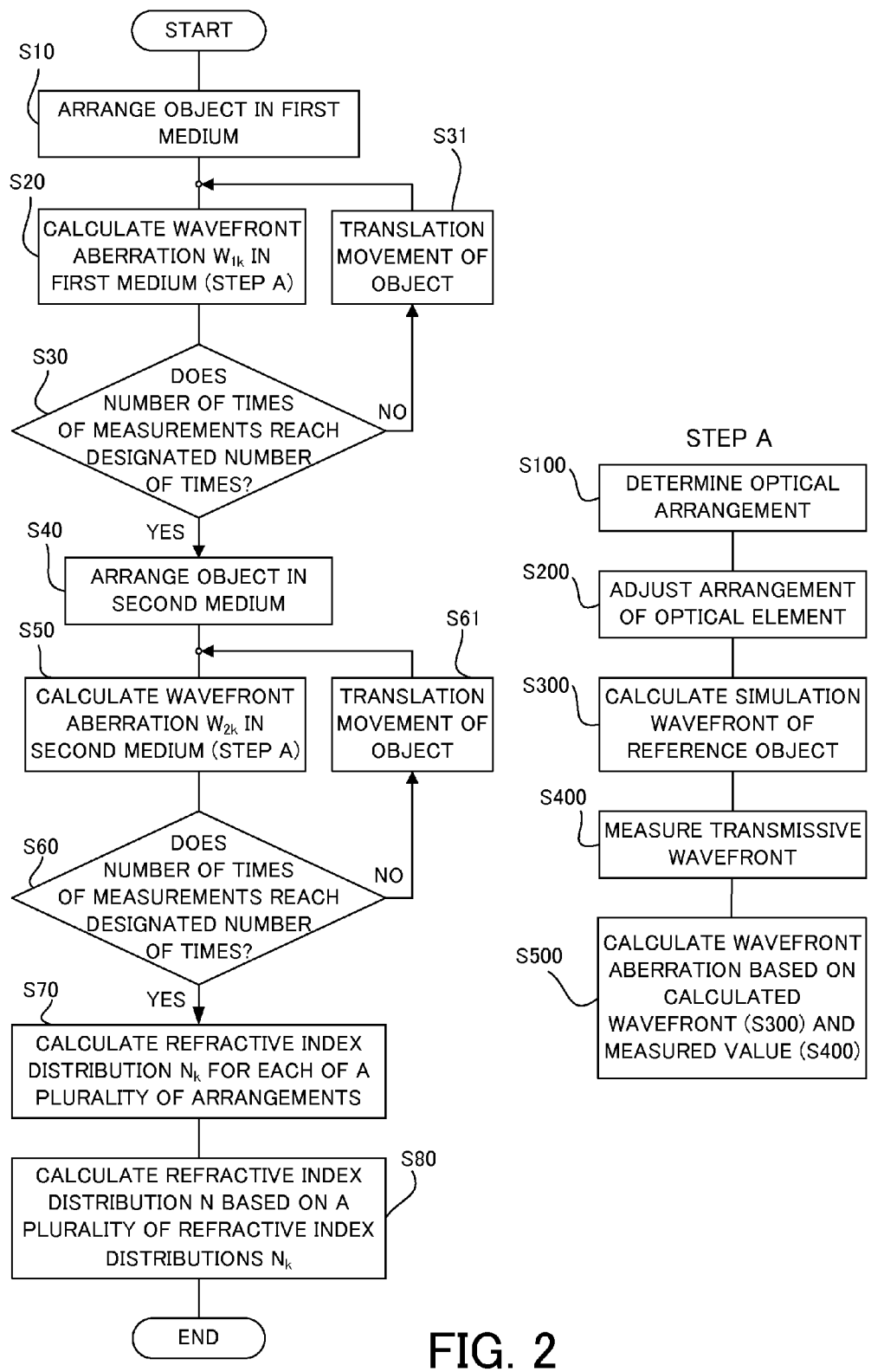
FIG. 2 is a flowchart of illustrating a method of measuring the refractive index distribution in Embodiment 1.

FIG. 2 is a flowchart of illustrating a procedure of process of calculating the refractive index distribution of the object 50, "S" is an abbreviation for "Step". The calculation process of the present embodiment is performed by a computer 80 (a processing unit) illustrated in FIGS. 1A and 1B in accordance with a program.

First of all, as illustrated in FIG. 1A, the object 50 is disposed (arranged) in the object case 51 filled with the first medium (for example water) (S10). Next, in accordance with Step A, a wavefront aberration $W_{1k}$ (a first wavefront aberration) for the first medium is calculated (S20). Symbol k denotes a number of times of measurements (a number of indicating k-th measurement).

In Step A, first of all, an optical arrangement of each element is determined (S100). The optical arrangement means arrangements of the pinhole 20, the collimator lens 40, the collimator lens 41, the object case 51, the object 50, and the Shack-Hartmann sensor 60 in the optical axis direction and a direction perpendicular to the optical axis. It is preferred that the optical arrangement is an arrangement where an angle of the light entering the Shack-Hartmann sensor 60 with respect to the optical axis is small, i.e. an arrangement where the light is close to parallel light.

FIG. 1A illustrates the arrangement where a center of each element is disposed on the optical axis. The outer light of the convergent light emitted from the collimator lens 41 does not enter the object 50 and is blocked by the edge portion of the object 50.

Next, the arrangement of each element is adjusted in accordance with the determined optical arrangement (S200). The adjustment of the arrangement is performed by relatively moving on a rail (not shown). Then, a simulation wavefront $W_{sim1k}$ of a reference object that has the same shape as the object 50 and that has a specific refractive index distribution is calculated (S300). This step is a step in which the object (the reference object) having a uniform refractive index distribution is assumed so as to calculate a transmissive wavefront in the same state as that in S200. The term of the same shape as the object 50 means a design value of the object 50 or a measured value that is obtained by a measurement in a different step. Instead of the simulation, a reference object that has the same shape as the object 50 and that does not have a refractive index distribution is actually manufactured by grinding, polishing, or the like, so that the transmissive wavefront may be measured by using the apparatus illustrated in FIGS. 1A and 1B.

The simulation wavefront (the transmissive wavefront) $W_{sim1k}$ of the reference object in the first medium at a point (x,y) inside the object 50 illustrated in FIG. 3A is represented by the following Expression (1). In the embodiment, in order to simplify Expression (1), a thickness of a side surface of the object case 51 is ignored.

$$W_{sim1k} = L_{a1k}(x/y) + n_1 L_{b1k}(x,y) + N_0 L_{1k}(x,y) + n_1 L_{c1k}(x,y) + L_{d1k}(x,y) \quad (1)$$

In Expression (1), symbols $L_{a1k}(x,y)$, $L_{b1k}(x,y)$, $L_{c1k}(x,y)$, and $L_{d1k}(x,y)$ are geometric distances between respective elements illustrated in FIG. 3B in a traveling direction of the ray. The ray of FIG. 3B indicates a ray which passes through the point (x,y) in the object 50 illustrated in FIG. 3A. Symbol $L_{1k}(x,y)$ is a geometric length of the optical path of the ray in the object 50, i.e. a thickness of the object 50 along the ray. Symbol $L_{1k}(x,y)$ can be calculated by a ray trace using the reference object. Therefore, when calculating $W_{sim1k}$, $L_{1k}(x,y)$ at an arbitrary point may also be calculated. Symbol $n_1$ is a refractive index of the first medium (a first refractive index), and symbol $N_0$ is a refractive index of the reference object.

Next, the transmissive wavefront $W_{m1k}$ (a first transmissive wavefront) of the object 50 is measured (S400). The first transmissive wavefront $W_{m1k}$ is represented as the following Expression (2) using the geometric distance of FIG. 3B.

$$W_{m1k} = L_{a1k}(x, y) + n_1 L_{b1k}(x, y) + N_k(x, y)[L_{1k}(x, y) + dL_k(x, y)] + n_1[L_{c1k}(x, y) - dL_k(x, y)] + L_{d1k}(x, y) \quad (2)$$

Symbol $N_k(x,y)$ is a refractive index that is averaged in the traveling direction of the ray illustrated in FIG. 3B. Symbol $dL_k(x,y)$ is a thickness error (a shape error) on the basis of the design value of the object 50 in the traveling direction of the ray. Symbols $L_{a1k}(x,y)$, $L_{b1k}(x,y)$, $L_{c1k}(x,y)$, $L_{d1k}(x,y)$, and $L_{1k}(x,y)$ in each of Expressions (1) and (2) use the same values each other. This is because a difference of the optical paths in a case where the refractive index distribution exists and in a case where the refractive index distribution does not exist is small enough to be ignored.

The wavefront aberration that corresponds to a difference between the transmissive wavefront $W_{sim1k}$ of the reference object obtained in S300 and the first transmissive wavefront $W_{m1k}$ obtained in S400 is calculated as represented by the following Expression (3).

$$W_{m1k} - W_{sim1k} = (N_k(x,y) - N_0) L_{1k}(x,y) + (N_k(x,y) - n_1) dL_k(x,y) \quad (3)$$

Then, an approximation represented by the following Expression (4) is performed so as to calculate the wavefront aberration $W_{1k}$ in the first medium as represented by Expression (5) (S500).

$$(N_k(x,y) - N_0) dL_k(x,y) \sim 0 \quad (4)$$

$$W_{1k} = (N_k(x,y) - N_0) L_{1k}(x,y) + (N_0 - n_1) dL_k(x,y) \quad (5)$$

The measurement result of the transmissive wavefront $W_{m1k}$ obtained in S400 contains the refractive index distribution of the object 50, influences of the object shape and the error of the object shape, and an offset caused by the measurement system. The transmissive wavefront $W_{sim1k}$ of the reference object is subtracted from the transmissive wavefront $W_{m1k}$, and thus the influence of the object shape and the offset caused by the measurement system are compensated. As a result, in S500, the wavefront aberration $W_{1k}$ is obtained so that information of the refractive index distribution $N_k(x,y)$ of the object 50 that is a residual error and the influence of the error of the object shape are obtained.

The refractive index distribution $N_k(x,y)$ is a value that is averaged in a transmitting direction of the ray in the object at the time of the k-th measurement. In order to obtain a refractive index distribution $N(x, y, z)$ over the whole region of the effective diameter of the object, refractive index distributions measured in a plurality of transmitting directions of the rays are necessary. Generally, the object is rotated with respect to incident light, and thus the refractive index distribution over the whole region of the effective diameter of the object can be obtained. However, it is difficult to manufacture a high-accuracy rotating mechanism and also its cost is high. In addition, since the shape of the object is different from the design value, it is difficult to specify a position or an inclination of the object with high accuracy when rotating the object. Accordingly, in the present embodiment, a translation movement of the object is performed with respect to the light entering at different angles so as to obtain the effect similar to rotating the object. Compared to the rotational movement, the translation movement is easily controlled and a position is also easily specified, and an apparatus can be provided at low cost.

In S30, it is determined whether the number k of times of measurements reaches a designated number m of times. When the number k of times of measurements does not reach the designated number m of times (k<m), the translation movement of the object 50 is performed so as to make a different arrangement (S31), and then, the flow returns to S20. On the other hand, when the number k of times of measurements reaches the designated number m of times, the flow moves to the measurement of the second medium (S40).

FIG. 1B illustrates an arrangement where the translation movement of the object 50 is performed in a direction perpendicular to the optical axis. The translation movement enables the ray blocked by the edge portion of the object 50 in FIG. 1A to enter the object 50. As a result, the refractive index distributions in the transmitting directions different from each other can be measured.

In the present embodiment, as illustrated in FIG. 1B, the translation movement is performed for the object case 51 containing the object 50 and the medium. In other words, the translation movement of the object 50 is performed by moving the object case 51 containing the object 50 and the medium with respect to the reference light 30. The object case 51 containing the object 50 is moved, and thus the optical arrangement of the object 50 and the object case 51 can be maintained. In other words, the error of the optical arrangement for both the object 50 and the object case 51 due to the translation movement does not occur. In addition, the object 50 is fixed with respect to the medium, i.e. there is no relative displacement between the object 50 and the medium, and therefore the generation of the refractive index distribution of the medium caused by flow of the medium can be prevented. The translation movement is performed for the object case 51 as well as the object 50, and therefore the accuracy of the measurement can be improved. In addition, the translation movement is performed for the object case 51 as well as the object 50, and therefore a moving mechanism is simplified and the cost of the apparatus can be reduced.

The designated number m of times is different in accordance with the shape of the object or the refractive index distribution. When the shape of the object 50 is rotationally symmetric around the optical axis and also the refractive index distribution is rotationally symmetric around the optical axis, the number m of times of measurements may also be twice. The two measurement arrangements are for example an arrangement where the optical axis coincides with a rotationally-symmetric axis of the object 50 and an arrangement where the optical axis does not coincide with the rotationally-symmetric axis of the object 50.

Subsequently, the object 50 is disposed (arranged) inside the object case 51 filled with the second medium (for example oil) (S40). The object case 51 may be the same case as that for the first medium or another case may also be prepared.

Next, in accordance with Step A similarly to S20, a wavefront aberration $W_{2k}$ (a second wavefront aberration) in the second medium is calculated based on the transmissive wavefront $W_{sim2k}$ of the reference object and the second transmissive wavefront $W_{m2k}$ of the object (Step S50). The second wavefront aberration $W_{2k}$ in the second medium is represented as the following Expression (6).

$$W_{2k}=(N_k(x,y)-N_0)L_{2k}(x,y)+(N_0-n_2)dL_k(x,y) \quad (6)$$

In Expression (6), symbol $n_2$ is a refractive index (a second refractive index) of the second medium, Symbol $L_{2k}(x,y)$ is a geometric length of the optical path of the ray passing through the coordinate (x,y) in the second medium, i.e. a thickness of the object 50 along the ray. Symbol $L_{2k}(x,y)$ can also be calculated by the ray trace when calculating the transmissive wavefront $W_{sim2k}$ of the reference object. It is difficult to match the optical paths of the rays passing through the coordinate (x,y) in the first medium and the second medium, and therefore $L_{1k}(x,y)$ and $L_{2k}(x,y)$ are commonly different from each other. On the other hand, the shape error $dL_k(x,y)$ is an extremely small value compared to $L_{1k}(x,y)$ and $L_{2k}(x,y)$. Accordingly, there is no problem when the same value is used for the first medium and the second medium.

In S60, similarly to S30, it is determined whether the number k of times of measurements reaches a designated number m of times. When the number k of times of measurements does not reach the designated number m of times (k<m), the translation movement of the object 50 is performed so as to make a different arrangement (S61), and then the flow returns to S50. On the other hand, when the number k of times of measurements reaches the designated number m of times, the flow moves to S70 in which the refractive index distribution is obtained.

In S70, a refractive index distribution $N_k(x,y)$ for each of the plurality of arrangements is calculated. When the shape error $dL_k(x,y)$ is removed by using Expressions (5) and (6), the refractive index distribution $N_k(x,y)$ is represented by the following Expression (7).

$$N_k(x, y) = N_{02} + \frac{(N_0 - n_1)W_{2k} - (N_0 - n_2)W_{1k}}{n_2 - n_1} \cdot \frac{1}{L_{eff_k}(x, y)} \quad (7)$$

$$L_{eff_k}(x, y) = \frac{(N_0 - n_1)L_{2k}(x, y) - (N_0 - n_2)L_{1k}(x, y)}{n_2 - n_1}$$

In Expression (7), symbol $L_{eff_k}(x,y)$ means an effective thickness of the object 50 that is obtained based on $L_{1k}(x,y)$ and $L_{2k}(x,y)$. When $L_{1k}(x,y)$ is equal to $L_{2k}(x,y)$, i.e. the traveling directions of the rays in first and second media coincide with each other, $L_{eff_k}(x,y)$ is equal to $L_{1k}(x,y)$ and $L_{2k}(x,y)$. Substituting the effective thickness $L_{eff_k}(x,y)$ into Expression (7), a shape component is removed so as to obtain the refractive index distribution $N_k(x,y)$ (S70). The shape component means a combination of the effective thickness $L_{effk}(x,y)$ obtained from the design value of the object 50 and the shape error $dL_k(x,y)$.

Finally, the refractive index distribution $N(x, y, z)$ over the whole region of the effective diameter of the object is calculated based on the plurality of refractive index distributions $N_k(x,y)$ (S80). In the calculation of the refractive index distribution $N(x,y,z)$ over the whole region of the effective diameter of the object, a polynomial that expresses the refractive index distribution over the whole region of the effective diameter of the object may be assumed so as to reproduce the plurality of refractive index distributions $N_k(x,y)$ obtained by the polynomial.

The polynomial that represents the refractive index distribution $N(x,y,z)$ over the whole region of the effective diameter of the object is, for example represented by an entire function of xyz as the following Expression (8).

$$N(x, y, z) = a_1 + a_2 x + a_3 y + a_4 z + a_5 x^2 + a_6 y^2 + a_7 z^2 + \quad (8)$$
$$a_8 xy + a_9 yz + a_{10} zx + a_{11} x^3 + a_{12} y^3 + a_{13} z^3 + a_{14} x^2 y +$$
$$a_{15} y^2 z + a_{16} z^2 x + a_{17} xy^2 + a_{18} yz^2 + a_{19} zx^2 + a_{20} xyz$$

For example, when terms up to third order of Expression (8) is used, coefficients of the polynomial is represented by a column vector having 20 terms as the following Expression (9).

$$A = \begin{bmatrix} a_1 \\ a_2 \\ \vdots \\ a_{20} \end{bmatrix} \quad (9)$$

The refractive index distribution $N_k(x,y)$ is a refractive index which is averaged in the transmitting direction of the ray. In other words, the refractive index distribution $N_k(x,y)$ is a constant refractive index in the transmitting direction of the ray. Therefore, under the condition that the refractive index distribution is a constant refractive index, $N_k(x,y)$ can be expanded to a three-dimensional function as represented by $N_k(x,y,z)$. When the object 50 is divided into 100 regions, the refractive index distribution $N_k(x,y,z)$ expanded as a three-dimensional function is represented by the following Expression (10). Symbol $N_{1 \ldots m}(x,y,z)$ in the following Expression (11) is a vector that is obtained by combining the plurality of refractive index distributions (m refractive index distributions).

$$N_k(x, y, z) = \begin{bmatrix} N_k(x_{100(k-1)+1}, y_{100(k-1)+1}, z_{100(k-1)+1}) \\ N_k(x_{100(k-1)+2}, y_{100(k-1)+2}, z_{100(k-1)+2}) \\ \vdots \\ N_k(x_{100k}, y_{100k}, z_{100k}) \end{bmatrix} \quad (10)$$

$$N_{1 \ldots m}(x, y, z) = \begin{bmatrix} N_1(x, y, z) \\ N_2(x, y, z) \\ \vdots \\ N_m(x, y, z) \end{bmatrix} = \begin{bmatrix} N_1(x_1, y_1, z_1) \\ N_1(x_2, y_2, z_2) \\ \vdots \\ N_m(x_{100m}, y_{100m}, z_{100m}) \end{bmatrix} \quad (11)$$

In this case, when a coefficient vector A is obtained so as to satisfy the following Expression (12), each coefficient of the coefficient vector A is a coefficient that reproduces the plurality of refractive index distributions, which represents the refractive index distribution over the whole region of the effective diameter of the object. In Expression (12), symbol X is a matrix having 100 m rows and 20 columns that is represented by the following Expression (13).

$$N_{1 \ldots m}(x, y, z) = XA \quad (12)$$

$$X = \begin{bmatrix} 1 & x_1 & y_1 & z_1 & \cdots & x_1 y_1 z_1 \\ 1 & x_2 & y_2 & z_2 & \cdots & x_2 y_2 z_2 \\ \vdots & \vdots & \vdots & \vdots & \ddots & \vdots \\ 1 & x_{100m} & y_{100m} & z_{100m} & \cdots & x_{100m} y_{100m} z_{100m} \end{bmatrix} \quad (13)$$

When least squares method is used, $\phi$ is defined as represented by the following Expression (14) or (15) and each coefficient of the coefficient vector A is determined so as to minimize $\phi^2$. The embodiment is not limited to the least squares method, and other methods may also be used to obtain the coefficient vector A. Thus, the coefficient vector A of the polynomial that represents the refractive index distribution over the whole region of the effective diameter of the object is obtained, and the method of measuring the refractive index distribution in the present embodiment is finished.

$$\phi = N_{1 \ldots m}(x,y,z) - XA \quad (14)$$

$$\phi = A - X^{-1} N_{1 \ldots m}(x,y,z) \quad (15)$$

In the present embodiment, in the k-th measurement for the first medium and the second medium, the transmitting directions of the ray of FIG. 3B coincide with each other. However, wavefront aberration data in which the transmitting directions of the ray are matched for the first medium and the second medium only need to be used when the refractive index distribution is calculated in S70, and the order of the arrangement to be measured may be set for each medium at random. Alternatively, a measurement flow in which the translation movement of the object 50 is performed so as to make the different arrangements may be used after performing Steps S10 to S70 without containing Steps S30 and S60. In other words, this means that the calculation of the refractive index distribution is performed and then a measurement for the subsequent arrangement is performed.

In FIG. 1B, the translation movement of the object 50 is performed in the direction perpendicular to the optical axis, but the translation movement may be performed in a direction parallel to the optical axis or a combination of both the directions may also be used. Alternatively, the translation movement may be performed only for the object 50 without moving the object case 51. In this case, however, it is preferred that the measurement is performed after the flow of the medium caused by the movement of the object 50 is stopped.

In the present embodiment, instead of performing the translation movement of the object 50, the translation movement may be performed for an illumination optical system (the reference light 30) that is configured by the light source 10, the pinhole 20, the collimator lens 40, and the collimator lens 41. In other words, the translation movement of the object 50 in this case is performed by moving the illumination optical system (the reference light 30) in a state where the object 50 is fixed. The illumination optical system that emits the reference light 30 is moved, and thus an effect that is the same as that of the translation movement of the object 50 relative to the reference light 30 can be obtained. If the light emitted from the collimator lens 40 is parallel light, the translation movement of the collimator lens 41 only needs to be performed.

The Shack-Hartmann sensor 60 that is a wavefront measuring unit of the present embodiment has a structure of collecting the light entering a lens array onto a CCD. When an inclined transmissive wavefront enters the lens array, a position of a light collecting point on the CCD is displaced. Since the Shack-Hartmann sensor 60 can convert the inclination of the transmissive wavefront into the position displacement of the light collecting point to be measured, a wavefront having a large amount of aberration can be measured. In the present embodiment, if a measuring unit capable of detecting a gradient or an inclination of the wavefront as measurable physical quantity even in the transmissive wavefront having the large amount of aberration is used, the embodiment is not limited to the Shack-Hartmann sensor 60. For example, a measuring unit which uses Hartmann method, Shearing interferometer, or Ronchi test may also be used. The light source 10 is not limited to the semiconductor laser, and a common laser, an LED, or a halogen lamp may also be used. Instead of the pinhole 20 that generates the divergent light, the light from the light source 10 can be guided into a fiber so as to use emission light from the fiber.

When the refractive index distribution $N_k(x,y)$ is calculated using Expression (7), the refractive index of each of the first medium and the second medium is necessary. The refractive index of the medium is calculated by measuring a temperature of the medium in measuring the first and second transmissive wavefronts and then by using a relationship between the refractive index and the temperature (literature data or a measured value obtained by a measurement). Alternatively, the refractive index may be measured each time of the measurement. The refractive index of the medium can be measured by using a member having a known refractive index and a known shape of a wedge shape (for example, a glass prism). Specifically, the prism is immersed in the medium and the reference light enters the prism so as to measure the transmissive wavefront. The refractive index of the medium may be calculated based on information of the inclination of the wavefront and the refractive index and the shape of the prism. The refractive index of the medium can also be measured by using a low-coherence interference method or the like.

In the present embodiment, as a combination of the first and second media, the combination of water and oil is used. However, the present embodiment is not limited to this, and other combinations may also be applied if the media have refractive indices different from each other. The medium may also be gas or solid. For example, air and water, air and oil, or two kinds of oils having refractive indices different from each other may be used. The two kinds of media may also be a medium which is made of the same material with a different refractive index depending on the change of the temperature. However, if the medium has ununiformity of the refractive index, the measurement accuracy is deteriorated. Therefore, it is preferred that a medium in which the refractive index is uniformly distributed is used.

In the present embodiment, the convergent light enters the object 50, but the divergent light or the parallel light may also enter the object 50. In particular, when a lens having a positive power is used, it is preferred that the object 50 is arranged so that the divergent light or the parallel light enters the object 50. For example, when the divergent light enters the object 50, the collimator lens 40 and the collimator lens 41 may be removed or the reference light 30 may be collected once between the collimator lens 41 and the object case 51. When the parallel light enters the object 50, the collimator lens 41 only has to be removed.

In the present embodiment, the method of measuring the refractive index distribution is described, but if only the influence after the light transmits through the object 50 needs to be evaluated, a wavefront aberration (an optical path length distribution) that corresponds to a product of the refractive index distribution $N_k(x,y)$ of Expression (7) and the effective thickness $L_{effk}(x,y)$ may be used. This is a wavefront aberration which represents the influence of the refractive index distribution. Accordingly, the method of measuring the refractive index distribution of the present embodiment includes a method of measuring the wavefront aberration that represents the influence of the refractive index distribution, as well as a method of measuring the refractive index value that is a non-dimensional amount.

As described above, the method of measuring the refractive index distribution of the present embodiment measures the transmissive wavefront by the reference light entering the object in two kinds of media having refractive indices different from each other and removing a shape component of the object based on the result so as to obtain the refractive index distribution. Then, the refractive index distributions are obtained with respect to a plurality of arrangements so as to calculate the refractive index distribution over a whole region of the effective diameter of the object. The plurality of arrangements are achieved by performing the translation movement of the object with respect to the reference light for each medium. Using the translation movement instead of a rotational movement, the work and the position control are easy, and therefore a configuration of an apparatus is simplified and the cost can be reduced. Since the object is fixed with respect to the medium, the refractive index distribution of the medium caused by the flow of the medium does not occur. Furthermore, the refractive index of the medium does not have to match the refractive index of the object. Accordingly, the method of measuring the refractive index distribution of the present embodiment can measure the refractive index distribution over the whole region of the effective diameter of the object with high accuracy.

[Embodiment 2]

Next, referring to FIGS. 4A, 4B, and 5, Embodiment 2 of the present invention will be described. FIGS. 4A and 4B are block diagrams of a measurement apparatus of a refractive index distribution in the present embodiment. The measurement apparatus of the refractive index distribution of the present embodiment, first of all, measures a transmissive wavefront by two kinds of reference lights (first wavelength light and second wavelength light) having wavelengths different from each other entering an object in a state where the object is immersed in a medium M (for example oil) having a refractive index different from a refractive index of the object (a measurement step). Subsequently, the apparatus uses the measurement result of the transmissive wavefront so as to calculate the refractive index distribution of the object (a calculation step). In this case, a translation movement of the object with respect to the reference light is performed so as to set a plurality of arrangements that are arrangements of the object different from each other and a refractive index distribution for each arrangement is obtained. Then, the refractive index distribution over a whole region of an effective diameter of the object is calculated based on the plurality of refractive index distributions corresponding to the plurality of arrangements. The configurations similar to those of Embodiment 1 will be described with the same symbols.

A side surface of the object case 51 at the side of the light source is made of a light transmissive member (for example a glass) that has curvature. The object case 51 contains the medium M and the object 50 that is held by the object supporting portion 52. The object case 51 includes a moving unit such as a stage capable of performing the translation movement. In the present embodiment, as the measuring unit of the transmissive wavefront, A Talbot interferometer is used.

As illustrated in FIGS. 4A and 4B, light emitted from a light source 10 (for example, HeNe laser) that emits the light having a first wavelength $\lambda_1$ transmits through a beam splitter 25 (for example, a dichroic mirror) and then reaches the pinhole 20. On the other hand, light emitted from a light source 11 (for example, HeCd laser) that emits the light having a second wavelength $\lambda_2$ is reflected by the beam splitter 25 and then reaches the pinhole 20. A direction of the emission of the light (light beam) of the light source 10 is referred to as an optical axis direction, and a center of the light beam is referred to as an optical axis.

The reference light 30 that passes through the pinhole 20 to be divergent light passes through the collimator lens 40 and the collimator lens 41 to be convergent light. The reference light 30 that is the convergent light passes through the side surface of the object case 51 and the medium M to enter the object 50. The light passing through the object 50 passes through a diffraction grating 70 that is a two-dimensional orthogonal grid, and then is imaged (measured) by an image pickup element 61 (for example, a CCD sensor or a CMOS sensor) that is a detector. When an angle of the transmitted light that transmits through the object 50 with respect to the optical axis is small, a self-image of the diffraction grating 70 is obtained on the image pickup element 61 as an interference fringe if a distance Z between the diffraction grating 70 and the image pickup element 61 satisfies Talbot condition that is represented by the following Expression (16).

$$\frac{Z_0 Z}{Z_0 - Z} = \frac{md^2}{\lambda} \quad (16)$$

In Expression (16), symbol Z is a distance between the diffraction grating 70 and the image pickup element 61, which is called Talbot distance in the embodiment. Symbol m is a natural number, symbol d is a grating period of the diffraction grating 70, and $Z_0$ is a distance from the diffraction grating 70 to an image plane of the object 50. The distance $Z_0$ is positive in a direction from the diffraction grating 70 toward the image pickup element 61. The grating period d of the diffraction grating 70 is determined in accordance with an amount of the aberration of the object 50 and a pixel size of the image pickup element 61.

Figure 5:
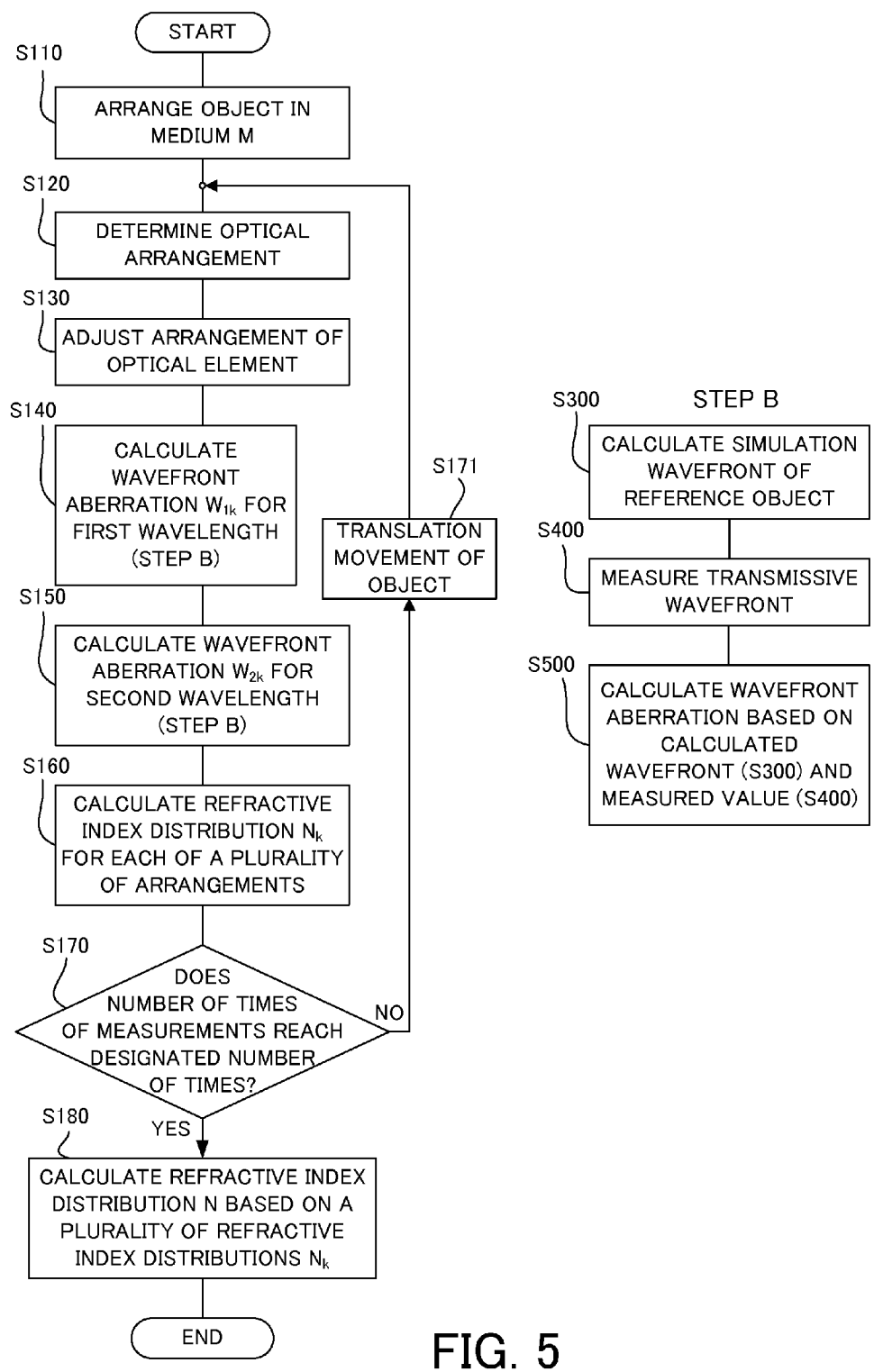
FIG. 5 is a flowchart of illustrating a method of measuring the refractive index distribution in Embodiment 2.

FIG. 5 is a flowchart of illustrating a procedure of a process of calculating the refractive index distribution of the object 50 in the present embodiment. First of all, as illustrated in FIG. 4A, the object case 51 is filled with the medium M, and the object 50 is disposed (arranged) in the medium M (S110). Next, an optical arrangement of each element is determined (S120). Then, the arrangement of each element is adjusted in accordance with the determined optical arrangement (S130). Subsequently, the wavefront aberration $W_{1k}$ for the first wavelength is calculated in accordance with Step B (S140).

In Step B, first of all, a simulation wavefront $W_{sim1k}$ of a reference object that has the same shape as that of the object 50 and that has a specific refractive index distribution is calculated (S300). Next, the reference light 30 having the first wavelength enters the object 50 so as to measure a transmissive wavefront $W_{m1k}$ (a first transmissive wavefront) (S400). When the first transmissive wavefront of the first wavelength is measured, the mixture of the light having a second wavelength is prevented. In the present embodiment, the light source 11 is set to OFF, or a shutter or the like is inserted between the light source 11 and the beam splitter 25. Alternatively, a wavelength selective filter through which the light having the second wavelength does not transmit or the like is inserted between the beam splitter 25 and the pinhole 20.

This step includes obtaining an image of an interference fringe by the image pickup element 61 and performing an image restoration processing of the transmissive wavefront by a computer 80. The image restoration processing of the transmissive wavefront (hereinafter, referred to as a wavefront restoration) is performed by an FFT method (fast Fourier transform). The wavefront restoration by the FFT method is a method of separating a carrier fringe and an aberration using a property that the aberration disturbs the carrier fringe of the interference fringe. Specifically, a two-dimensional FFT is performed for the interference fringe so as to be converted into a frequency map. Next, the carrier frequency or its periphery part in the frequency map is only clipped and a coordinate transformation is performed so that the carrier frequency is at the origin, and then an iFFT (inverse fast Fourier transform) is performed. Thus, a phase term of a complex amplitude map is obtained. As a result, the obtained phase map is the transmissive wavefront.

Then, the wavefront aberration $W_{1k}$ for the first wavelength is calculated based on the transmissive wavefront $W_{sim1k}$ of the reference object and the first transmissive wavefront $W_{m1k}$ (S500). The wavefront aberration $W_{1k}$ is represented by the following Expression (17).

$$W_{1k} = (N_{1k}(x,y) - N_{01})L_{1k}(x,y) + (N_{01} - n_1)dL_k(x,y) \quad (17)$$

In Expression (17), symbol $N_{1k}(x,y)$ is a refractive index for the first wavelength that is averaged in the traveling direction of the ray. Symbol $N_{01}$ is a refractive index of the reference object for the first wavelength.

Subsequently, the wavefront aberration $W_{2k}$ for the second wavelength is calculated in accordance with Step B (S150) similarly to the case of the first wavelength. When the second transmissive wavefront of the second wavelength is measured, the mixture of the light having the first wavelength is prevented. For example, the light source 10 is set to OFF, or a shutter or the like is inserted between the light source 10 and the beam splitter 25. Alternatively, a wavelength selective filter through which the light having the first wavelength does not transmit or the like is inserted between the beam splitter 25 and the pinhole 20. The wavefront aberration $W_{2k}$ is represented by the following Expression (18).

$$W_{2k} = (N_{2k}(X/y) - N_{02})L_{2k}(x,y) + (N_{02} - n_2)dL_k(x,y) \quad (18)$$

In Expression (18), symbol $N_{2k}(x,y)$ is a refractive index for the second wavelength that is averaged in the traveling direction of the ray. Symbol $N_{02}$ is a refractive index of the reference object for the second wavelength.

In the present embodiment, in S140 and S150, the wavefront aberration $W_{1k}$ and the wavefront aberration $W_{2k}$ are calculated in the same arrangement. However, the determination step of the optical arrangement for the second wavelength (S120) and the arrangement adjusting step of the optical element (S130) may also be inserted before S150.

A wavelength dependency of the refractive index at a coordinate (x,y) in the object 50 is also distributed in accordance with the refractive index distribution. Symbols $N_{1k}(x,y)$ and $N_{2k}(x,y)$ are linked by the following Expression (19) that is an approximate expression.

$$N_{2k}(x, y) - N_{1k}(x, y) = \frac{1}{A}(N_{2k}(x, y) - 1) \quad (19)$$

$$A = \frac{N_{r02} - 1}{N_{r02} - N_{r01}}$$

In Expression (19), symbols $N_{r01}$ and $N_{r02}$ are refractive indices of a glass material for each of the first wavelength and the second wavelength, respectively. These refractive indices may use literature data or measured values.

Using Expression (19), the refractive index distribution $N_{1k}(x,y)$ for the first wavelength and the refractive index distribution $N_{2k}(x,y)$ for the second wavelength are linked by the following Expression (20).

$$N_{2k}(x, y) - N_{02} = \frac{N_{r02} - 1}{N_{r01} - 1}(N_{1k}(x, y) - N_{01}) \quad (20)$$

A shape error $dL_k(x,y)$ of the object 50 is removed from the wavefront aberration $W_{1k}$ for the first wavelength in Expression (17) and the wavefront aberration $W_{2k}$ for the second wavelength in Expression (18). Furthermore, using Expression (20), Expression (21) that extracts the refractive index distribution $N_{1k}(x,y)$ of the object 50 for the first wavelength is introduced as follows.

$$N_{1k}(x, y) = N_{01} + \frac{(N_{01} - n_1)W_{2k} - (N_{02} - n_2)W_{1k}}{\frac{N_{r02} - 1}{N_{r01} - 1}(N_{01} - n_1) - (N_{02} - n_2)} \cdot \frac{1}{L_{effk}(x, y)} \quad (21)$$

$$L_{effk}(x, y) = \frac{(N_{r02} - 1)(N_{01} - n_1)L_{2k}(x, y) - (N_{r01} - 1)(N_{02} - n_2)L_{1k}(x, y)}{(N_{r02} - 1)(N_{01} - n_1) - (N_{r01} - 1)(N_{02} - n_2)}$$

The wavefront aberration $W_{1k}$ for the first wavelength obtained in S140, the wavefront aberration $W_{2k}$ for the second wavelength obtained in S150, and the effective thickness $L_{effk}(x,y)$ are substituted into Expression (21). As a result, the shape component is removed and the refractive index distribution $N_{1k}(x,y)$ of the object 50 for the first wavelength is calculated (S160). When the refractive index distribution $N_{2k}(x,y)$ of the object 50 for the second wavelength is calculated, the obtained refractive index distribution $N_{1k}(x,y)$ may be substituted into Expression (20).

In S170, it is determined whether the number k of times of measurements reaches the designated number m of times. When the number k of times of measurements does not reach the designated number m of times (k<m), the translation movement of both the object 50 and the object case 51 is collectively performed so as to make a difference arrangement (S171), and the flow returns to S120. On the other hand, when the number k of times of measurements reaches the designated number m of times, the calculation of the refractive index distribution N is performed (S180). In the present embodiment, the two arrangements illustrated in FIGS. 4A and 4B are set as measurement arrangements, i.e. the designated number of times is set to two (m=2).

FIG. 4B illustrates the arrangement in which the translation movement of both the object 50 and the object case 51 is collectively performed in a direction parallel to the optical axis. The ray blocked by the edge portion of the object 50 in FIG. 4A transmits in the arrangement of FIG. 4B. As a result, the refractive index distribution over the whole region of the effective diameter of the object 50 can be calculated.

In S180, the refractive index distribution $N_1(x,y)$ over the whole region of the effective diameter of the object 50 is calculated based on the plurality of refractive index distributions $N_{1k}(x,y)$. Considering the refractive index distribution $N_{11}(x,y)$ obtained by the arrangement in FIG. 4A, regions in lacking are complemented by using the refractive index distribution $N_{12}(x,y)$ obtained by the arrangement in FIG. 4B. In other words, an outer refractive index distribution is connected to the inner refractive index distribution of $N_{11}(x,y)$ by using $N_{12}(x,y)$. This connection can be performed by using a coefficient of a polynomial, similarly to Embodiment 1. By performing this step, the method of measuring the refractive index distribution in the present embodiment is finished.

The refractive index distribution over the whole region of the effective diameter of the object 50 can be calculated without using the two kinds of arrangements of FIGS. 4A and 4B as described in the present embodiment, i.e. can be calculated only by the measurement in the arrangement of FIG. 4B. As illustrated in FIG. 4B, however, when a ray angle of the light entering the Talbot interferometer is large, the error of the wavefront measurement is increased and the calculation accuracy of the refractive index distribution is deteriorated. Accordingly, in order to measure the refractive index distribution with high accuracy, as described in the present embodiment, most of parts in the effective diameter of the object 50 is measured by the optical arrangement as illustrated in FIG. 4A and only the remaining peripheral part may be complemented by the measurement in the optical arrangement of FIG. 4B.

In the present embodiment, as illustrated in FIGS. 4A and 4B, the side surface of the object case 51 at the side of the light source has curvature. When the side surface at the side of the light source is a plane plate, an incident angle of the reference light 30 entering the object 50 (an angle with respect to the optical axis) is decreased since the ray is refracted at a boundary. When the incident angle is decreased, there is a case where the ray passing through the whole region of the effective diameter of the object 50 does not exist even when the translation movement is performed as illustrated in FIG. 4B. When the side surface is the plane plate, an spherical aberration of the transmissive wavefront is increased and the accuracy of the wavefront measurement is deteriorated since a large amount of spherical aberration is generated in the reference light 30. Accordingly, it is preferred that a radius of curvature of the side surface is close to a radius of curvature of the wavefront of the reference light 30 so that the ray angle of the reference light 30 does not practically change in accordance with the refraction. Since the radius of curvature of the wavefront of the reference light 30 changes in accordance with a distance from the collimator lens 41, the radius of curvature of the side surface needs to be designed considering the arrangement of the object case 51. However, since an amount of change of the ray angle related to the arrangement error of the object case 51 is small, an exact arrangement does not have to be required. In the present embodiment, similarly to Embodiment 1, the translation movement is collectively performed for both the object 50 and the object case 51, or alternatively, the translation movement may be performed only for the object 50.

In the present embodiment, as light sources that output the lights having the first wavelength and the second wavelength, two kinds of light sources are prepared. However, the lights having two kinds of wavelengths may also be obtained by using one wavelength-variable light source such as a semiconductor laser, or the lights having two kinds of wavelengths may be generated by the combination of a broadband light source such as a supercontinuum light source and a narrowband filter. Since the Shearing interference method or the Hartmann method is used, an incoherent light source such as a halogen lamp can also be used as the broadband light source.

The measurement result by the measurement apparatus of the refractive index distribution (the method of measuring the refractive index distribution) described in each of Embodiments 1 and 2 can be fed back to a method of manufacturing an optical element. This method of manufacturing the optical element includes a step of molding the optical element based on the designed optical element, a step of measuring a shape of molded optical element so as to evaluate a shape accuracy, and a step of evaluating an optical performance of the optical element that satisfies the shape accuracy. Then, the method of measuring the refractive index distribution of the present embodiment can be applied to the step of evaluating the optical performance. When the evaluated optical performance does not satisfy a required specification, an amount of correcting an optical surface of the optical element is calculated, and the optical element is redesigned using the result. On the other hand, when the required specification is satisfied, the optical element is churned out. Thus, the measurement apparatus of the refractive index distribution of each embodiment can be applied to a usage of manufacturing the optical element.

According to a method of manufacturing the optical element of each embodiment described above, a refractive index distribution of the optical element can be measured with high accuracy, and therefore the optical element can be churned out by molding even when the optical element uses a glass material having a high refractive index.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-154073, filed on Jul. 9, 2012, which is hereby incorporated by reference herein in its entirety.

What is claimed is:

1. A method of measuring a refractive index distribution, the method comprising:
   a measurement step of arranging an object in a medium having a refractive index different from a refractive index of the object to measure a transmissive wavefront of the object by introducing reference light into the object, the reference light including rays of different angles and having a light beam diameter larger than an effective diameter of at least one of a light incident surface or a light emitting surface of the object; and
   a calculation step of calculating a refractive index distribution of the object using a measurement result of the transmissive wavefront,
   wherein the measurement step includes the steps of:
      performing a translation movement of the object or an illumination optical system that emits the reference light without rotating the object to dispose the object at different positions relative to the illumination optical system from each other, and
      measuring, for each of the different positions, a first transmissive wavefront in a first medium having a first refractive index and a second transmissive wavefront in a second medium having a second refractive index different from the first refractive index, and
   wherein the calculation step includes the steps of:
      calculating, for each of the different positions, a first wavefront aberration, which is a difference between a measurement result of the first transmissive wavefront and a transmissive wavefront obtained with a reference object having a specific refractive index distribution and the same shape as a shape of the object in the first medium,
      calculating, for each of the different positions, a second wavefront aberration, which is a difference between a measurement result of the second transmissive wavefront and a transmissive wavefront obtained with the reference object in the second medium, and
      calculating a plurality of refractive index distributions of the object corresponding to the different positions by removing a shape component of the object based on the first wavefront aberration and the second wavefront aberration to calculate the refractive index distribution of the object.

2. The method of measuring the refractive index distribution according to claim 1, wherein the measurement step performs the translation movement of an object case that contains the object and the medium relative to the illumination optical system.

3. The method of measuring the refractive index distribution according to claim 1, wherein the measurement step performs the translation movement of the illumination optical system that emits the reference light while the object is fixed.

4. The method of measuring the refractive index distribution according to claim 1, wherein the refractive index distribution calculated in the calculation step is a refractive index distribution over an entire region of an effective diameter of the object.

5. The method of measuring the refractive index distribution according to claim 1, wherein the refractive index distribution calculated in the calculation step is a three-dimensional refractive index distribution of the object.

6. A method of measuring a refractive index distribution, the method comprising:
   a measurement step of arranging an object in a medium having a refractive index different from a refractive index of the object to measure a transmissive wavefront of the object by introducing reference light into the object, the reference light including rays of different angles and having a light beam diameter larger than an effective diameter of at least one of a light incident surface or a light emitting surface of the object; and
   a calculation step of calculating a refractive index distribution of the object using a measurement result of the transmissive wavefront,
   wherein the measurement step includes the steps of:
      performing a translation movement of the object or an illumination optical system that emits the reference light without rotating the object to dispose the object at different positions relative to the illumination optical system from each other, and
      measuring, for each of the different positions, a first transmissive wavefront for a first wavelength and a second transmissive wavefront for a second wavelength different from the first wavelength, and
   wherein the calculation step includes the steps of:
      calculating, for each of the different positions, a first wavefront aberration, which is a difference between a measurement result of the first transmissive wavefront and a transmissive wavefront for the first wavelength obtained with a reference object having a specific refractive index distribution and the same shape as a shape of the object in the medium,
      calculating, for each of the different positions, a second wavefront aberration, which is a difference between a measurement result of the second transmissive wavefront and a transmissive wavefront for the second wavelength obtained with the reference object in the medium, and
calculating a plurality of refractive index distributions of the object corresponding to the different positions by removing a shape component of the object based on the first wavefront aberration and the second wavefront aberration to calculate the refractive index distribution of the object.

7. The method of measuring the refractive index distribution according to claim 6, wherein the measurement step performs the translation movement of an object case that contains the object and the medium relative to the illumination optical system.

8. The method of measuring the refractive index distribution according to claim 6, wherein the measurement step performs the translation movement of the illumination optical system that emits the reference light while the object is fixed.

9. The method of measuring the refractive index distribution according to claim 6, wherein the refractive index distribution calculated in the calculation step is a refractive index distribution over an entire region of an effective diameter of the object.

10. The method of measuring the refractive index distribution according to claim 6, wherein the refractive index distribution calculated in the calculation step is a three-dimensional refractive index distribution of the object.

11. A method of manufacturing an optical element, the method comprising the steps of:
molding the optical element; and
measuring a refractive index distribution of the optical element to evaluate the molded optical element,
wherein refractive distribution of the optical element is measured by a method comprising:
a measurement step of arranging an object in a medium having a refractive index different from a refractive index of the object to measure a transmissive wavefront of the object by introducing reference light into the object, the reference light including rays of different angles and having a light beam diameter larger than an effective diameter of at least one of a light incident surface or a light emitting surface of the object; and
a calculation step of calculating a refractive index distribution of the object using a measurement result of the transmissive wavefront,
wherein the measurement step includes the steps of:
performing a translation movement of the object or an illumination optical system that emits the reference light without rotating the object to dispose the object at different positions relative to the illumination optical system from each other, and
measuring, for each of the different positions, a first transmissive wavefront in a first medium having a first refractive index and a second transmissive wavefront in a second medium having a second refractive index different from the first refractive index, and wherein the calculation step includes the steps of:
calculating, for each of the different positions, a first wavefront aberration, which is a difference between a measurement result of the first transmissive wavefront and a transmissive wavefront obtained with a reference object having a specific refractive index distribution and the same shape as a shape of the object in the first medium,
calculating, for each of the different positions, a second wavefront aberration, which is a difference between a measurement result of the second transmissive wavefront and a transmissive wavefront obtained with the reference object in the second medium, and
calculating a plurality of refractive index distributions of the object corresponding to the different positions by removing a shape component of the object based on the first wavefront aberration and the second wavefront aberration to calculate the refractive index distribution of the object.

12. A method of manufacturing an optical element, the method comprising the steps of:
molding the optical element; and
measuring a refractive index distribution of the optical element to evaluate the molded optical element,
wherein refractive distribution of the optical element is measured by a method comprising:
a measurement step of arranging an object in a medium having a refractive index different from a refractive index of the object to measure a transmissive wavefront of the object by introducing reference light into the object, the reference light including rays of different angles and having a light beam diameter larger than an effective diameter of at least one of a light incident surface or a light emitting surface of the object; and
a calculation step of calculating a refractive index distribution of the object using a measurement result of the transmissive wavefront,
wherein the measurement step includes the steps of:
performing a translation movement of the object or an illumination optical system that emits the reference light without rotating the object to dispose the object at different positions relative to the illumination optical system from each other, and
measuring, for each of the different positions, a first transmissive wavefront for a first wavelength and a second transmissive wavefront for a second wavelength different from the first wavelength, and
wherein the calculation step includes the steps of:
calculating, for each of the different positions, a first wavefront aberration, which is a difference between a measurement result of the first transmissive wavefront and a transmissive wavefront for the first wavelength obtained with a reference object having a specific refractive index distribution and the same shape as a shape of the object in the medium,
calculating, for each of the different positions, a second wavefront aberration, which is a difference between a measurement result of the second transmissive wavefront and a transmissive wavefront for the second wavelength obtained with the reference object in the medium, and
calculating a plurality of refractive index distributions of the object corresponding to the different positions by removing a shape component of the object based on the first wavefront aberration and the second wavefront aberration to calculate the refractive index distribution of the object.

13. A measurement apparatus of a refractive index distribution, comprising:
an illumination optical system;
an object case configured to contain an object and a medium having a refractive index different from a refractive index of the object;

a moving unit configured to move, in a translation movement, at least one of the object or the illumination optical system;

a measuring unit configured to measure a transmissive wavefront of the object arranged in the medium by introducing reference light into the object, the reference light including rays of different angles and having a light beam diameter larger than an effective diameter of at least one of a light incident surface or a light emitting surface of the object; and a processing unit configured to obtain a refractive index distribution of the object based on the transmissive wavefront, wherein the moving unit is configured to move the object or the illumination optical system without rotating the object to dispose the object at different positions relative to the illumination optical system from each other, wherein the measuring unit is configured to measure a first transmissive wavefront in a first medium having a first refractive index and a second transmissive wavefront in a second medium having a second refractive index for the different positions, and wherein the processing unit is configured to:
  calculate, for each of the different positions, a first wavefront aberration, which is a difference between a measurement result of the first transmissive wavefront and a transmissive wavefront obtained with a reference object having a specific refractive index distribution and the same shape as a shape of the object in the first medium,
  calculate, for each of the different positions, a second wavefront aberration, which is a difference between a measurement result of the second transmissive wavefront and a transmissive wavefront obtained with the reference object in the second medium, and
  calculate a plurality of refractive index distributions of the object corresponding to the different positions by removing a shape component of the object based on the first wavefront aberration and the second wavefront aberration to calculate the refractive index distribution of the object.

14. The measurement apparatus of a refractive index distribution according to claim 13, wherein the object case comprises a curved light transmissive member facing the light source.

15. The measurement apparatus of a refractive index distribution according to claim 13, wherein the measuring unit includes a Hartmann sensor.

16. The measurement apparatus of a refractive index distribution according to claim 13, wherein the measuring unit includes a Shearing interferometer.

17. A measurement apparatus of a refractive index distribution, comprising:
  a light source configured to emit lights having first and second wavelengths that are different from each other;
  an object case configured to contain an object and a medium having a refractive index different from a refractive index of the object;
  a moving unit configured to move, in a translation movement the object or the illumination optical system;
  a measuring unit configured to measure a transmissive wavefront of the object arranged in the medium by introducing reference light into the object, the reference light including rays of different angles and having a light beam diameter larger than an effective diameter of at least one of a light incident surface or a light emitting surface of the object; and
  a processing unit configured to obtain a refractive index distribution of the object based on a first transmissive wavefront and a second transmissive wavefront measured using the first and second wavelengths respectively,
  wherein the moving unit is configured to move at least one of the object or the illumination optical system without rotating the object to dispose the object at different positions relative to the illumination optical system from each other,
  wherein the measuring unit is configured to measure, for each of the different positions, the first transmissive wavefront and the second transmissive wavefront,
  wherein the processing unit is configured to:
    calculate, for each of the different positions, a first wavefront aberration, which is a difference between a measurement result of the first transmissive wavefront and a transmissive wavefront for the first wavelength obtained with a reference object having a specific refractive index distribution and the same shape as a shape of the object in the medium,
    calculate, for each of the different positions, a second wavefront aberration, which is a difference between a measurement result of the second transmissive wavefront and a transmissive wavefront for the second wavelength obtained with the reference object in the medium, and
    calculate a plurality of refractive index distributions of the object corresponding to the different positions by removing a shape component of the object based on the first wavefront aberration and the second wavefront aberration to calculate the refractive index distribution of the object.

18. The measurement apparatus of a refractive index distribution according to claim 17, wherein the object case comprises a curved light transmissive member facing the light source.

19. The measurement apparatus of a refractive index distribution according to claim 17, wherein the measuring unit includes a Hartmann sensor.

20. The measurement apparatus of a refractive index distribution according to claim 17, wherein the measuring unit includes a Shearing interferometer.

* * * * *